(12) United States Patent
Elencwajg (10) Patent No.: US 8,000,809 B2
(45) Date of Patent: Aug. 16, 2011

(54) DEVICE FOR INTRACAVITY STIMULATION OF THE LEFT ATRIUM AND/OR VENTRICLE THROUGH ATRIAL TRANSSEPTAL PUNCTURE AND REMOVAL OF THE CATHETER PROXIMAL END BY THE RETROGRADE VENOUS ROUTE TOWARD THE PREPECTORAL REGION

(76) Inventor: Benjamin Daniel Elencwajg, Capital Federal (AR)

( * ) Notice: Subject to any disclaimer, the term of this patent is extended or adjusted under 35 U.S.C. 154(b) by 121 days.

(21) Appl. No.: 12/289,168

(22) Filed: Oct. 22, 2008

(65) Prior Publication Data

US 2010/0331939 A1    Dec. 30, 2010

(30) Foreign Application Priority Data

Oct. 23, 2007    (AR) .......................... P200701040682

(51) Int. Cl.
*A61N 1/372*    (2006.01)

(52) U.S. Cl. .......................... 607/122; 607/119; 600/374

(58) Field of Classification Search .................. 600/374, 600/508; 607/9, 119, 122
See application file for complete search history.

(56) References Cited

U.S. PATENT DOCUMENTS

| | | | | |
|---|---|---|---|---|
| 5,171,233 | A * | 12/1992 | Amplatz et al. | 604/540 |
| 6,016,811 | A * | 1/2000 | Knopp et al. | 128/898 |
| 6,254,610 | B1 * | 7/2001 | Darvish et al. | 606/108 |
| 6,430,426 | B2 * | 8/2002 | Avitall | 600/374 |
| 7,529,589 | B2 * | 5/2009 | Williams et al. | 607/119 |
| 2006/0224225 | A1 * | 10/2006 | Ransbury et al. | 607/122 |

\* cited by examiner

*Primary Examiner* — Carl H Layno
*Assistant Examiner* — Eugene Wu
(74) *Attorney, Agent, or Firm* — Allen, Dyer, Dopplet, Milbrath & Gilchrist, P.A.

(57) ABSTRACT

A device for intracavity stimulation of the left atrium and/or ventricle of the heart from the prepectoral region through a less invasive and lower-risk approach is provided that allows the implantation of an intracavity catheter in the left cardiac chambers through a femoral approach atrial transseptal puncture, and the removal of the catheter proximal end by the retrograde venous route.

4 Claims, 14 Drawing Sheets

DEVICE FOR INTRACAVITY STIMULATION OF THE LEFT ATRIUM AND/OR VENTRICLE THROUGH ATRIAL TRANSSEPTAL PUNCTURE AND REMOVAL OF THE CATHETER PROXIMAL END BY THE RETROGRADE VENOUS ROUTE TOWARD THE PREPECTORAL REGION

CROSS-REFERENCE TO RELATED APPLICATIONS

This application claims priority to Application Serial No. P 2007 01040682 filed in Argentina on Oct. 23, 2007, the disclosure of which is and incorporated by reference and commonly owned.

FIELD OF INVENTION

The invention generally relates to cardiac surgery and cardiac implantations, and more particularly to a device and method for intracavity stimulation of the left atrium and/or ventricle through a femoral approach atrial transseptal puncture and removal of the catheter proximal end by a retrograde venous route toward the prepectoral region.

BACKGROUND

Methods to insert catheters in left atrium and/or ventricles through surgery—an outer cut on the chest wall—, are well known and known to be a very sensitive and high-risk approach from a patients point of view and requires close post surgical control, or in the venous system of the heart, which method is often impossible to carry out and requires considerable expertise in performance, thus limiting general application. Currently, there exists an additional technique, which consists of intracavity stimulation of the left ventricle; however, it is complex and difficult to perform.

The insertion of catheters in right atrium and/or ventricles is currently performed in a simple way by inserting the catheter in the subclavian, cephalic or jugular vein after a simple puncture and by means of a catheter introducer.

However, this is not the case when the catheter is to be inserted in the left atrium and ventricle, because there is no direct path through the mentioned veins; as per the previous art, surgery is required in order to insert the catheter outside (the epicardial region) the atrium and/or the left ventricle, including a cut in the external chest wall, which procedure entails a great risk. On the other hand, this technique offers a very restricted access to the left atrium and ventricle, thus preventing the choice of the best implantation site.

There is the option to insert the catheter in the venous system of the heart, which is often impossible to perform due to the morphologic structure of the system, requiring considerable expertise in the technique and limiting its general application.

Another technique uses the transseptal puncture of the atrium to insert the catheter by the antegrade venous route. This technique requires multiple passing of sheaths, balloon catheters and lines through the interatrial septum, successive dilations of the interatrial septum, etc., which turn it complex and increase patients' risk.

SUMMARY

The present invention is directed to solving the problems as addressed above and in one embodiment provides a device for placing the catheter into (intracavity implantation) the left atrium and/or ventricle using the venous system, that is, without external surgical openings, only by making a single puncture on the septum between the right and left atria, and removal of the catheter proximal end (the end that is connected to the pacemaker or any other device that might be implanted) in the prepectoral region by the retrograde venous route.

A desirable feature of the invention is its simplicity and safety, since the elements are inserted by simple venous and transseptal punctures. Methods do not require a chest opening for implantation. Devices used do not require use of the venous system of the heart. The catheter is inserted into the left atrium and/or ventricle by a single transseptal puncture on the interatrial septum of the heart. There is no need for additional dilations of the interatrial septum puncture. Embodiments of the invention do not require successive passing of elements through the interatrial septum and allows the choice from among several sites of the best site on each patient to implant the catheter in the left atrium and ventricle. Further, the surgical techniques required are commonly used and broadly known.

One embodiment of the invention provides for the implantation of an intracavity catheter in the left atrium and/or ventricle through a single femoral approach transseptal puncture on the atrium, and the removal of the proximal end of the catheter by the retrograde venous route toward the prepectoral region.

BRIEF DESCRIPTION OF DRAWINGS

The advantages of this invention, which should not be limited to the brief description above, will become more apparent and the invention itself better understood by reference to the following embodiments of the invention herein described by way of example with reference to the accompanying annotated drawings in which.

In order to relate the drawings above to the following description, the parts or components shown in the different drawings have been identified with a common reference number.

DESCRIPTION OF EMBODIMENTS

Figure 1:
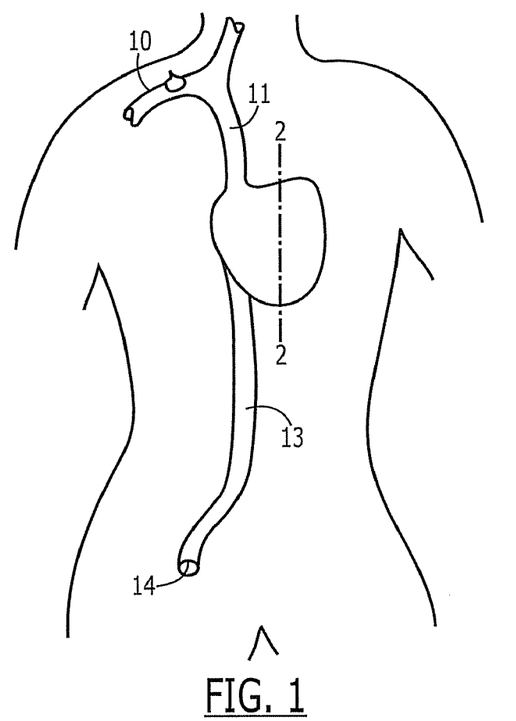
FIG. 1 is a schematic view of the human body with the localization of the subclavian vein and the femoral vein, and their relation to the superior vena cava, the inferior vena cava and the right atrium of the heart.
Figure 2:
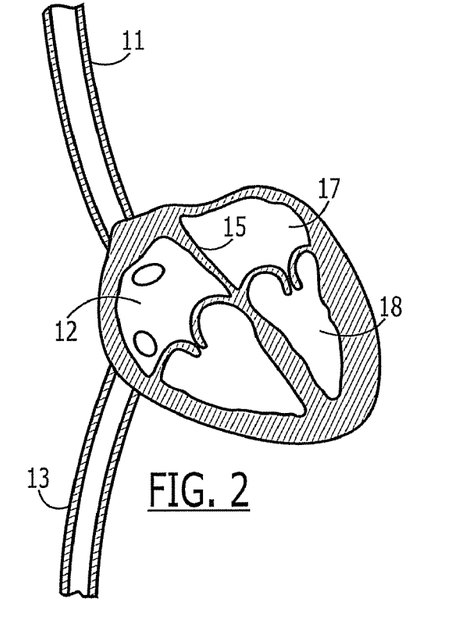
FIG. 2 is a 2-2 sectional view of FIG. 1 showing details of the cardiac chambers, and the superior vena cava and the inferior vena cava entry in the right atrium.
Figure 3:
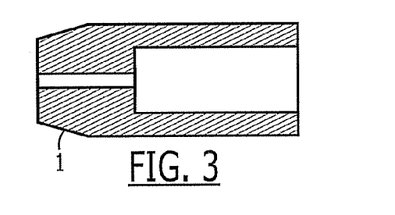
FIG. 3 is a longitudinal sectional view of a Fastener according to the teachings of the present invention, which is inserted by femoral route, showing the insertion site and the central passage.
Figure 4:
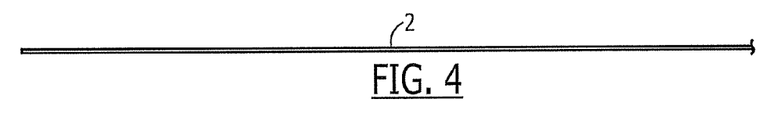
FIG. 4 is a side view of a Pulling Element of this according to the teachings of the present invention, which is inserted by femoral route.
Figure 5:
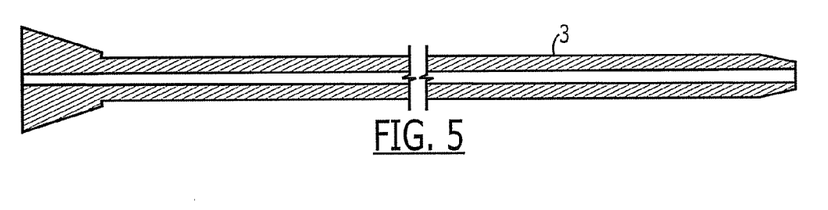
FIG. 5 is a longitudinal sectional view of a Runner according to the teachings of the present invention, which is inserted by femoral route, showing the central passage.
Figure 6:
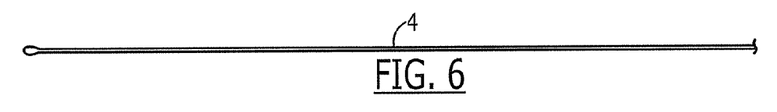
FIG. 6 is a side view of a Mandrel according to the teachings of the present invention, which is inserted by femoral route.
Figure 7:
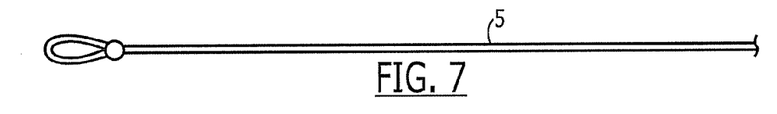
FIG. 7 is a side view of a Loop Catheter of this invention, which is inserted in the subclavian vein.
Figure 8:
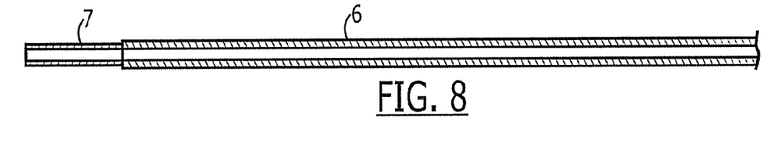
FIG. 8 is a side sectional view of a Cardiac Catheter of this invention, which is inserted by femoral route and removable by the subclavian, jugular or cephalic veins, showing the central passage.
Figure 9:
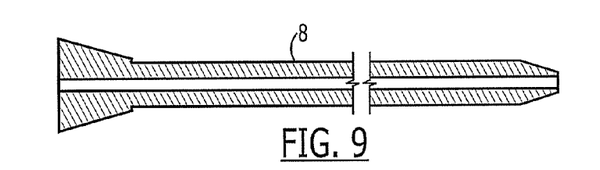
FIG. 9 is a longitudinal sectional view of an Aligning device of this invention and its central passage, which is inserted in the subclavian vein.

One embodiment of the invention is herein described by way of example as a system and method for intracavity stimulation of the left atrium and/or ventricle through a femoral approach atrial transseptal puncture and removal of a catheter proximal end by a retrograde venous route toward the prepectoral region. The system includes a KIT the following components that are assembled: a Fastener 1 (FIG. 3), a Pulling Element 2 (FIG. 4), a Runner 3 (FIG. 5), a Mandrel 4 (FIG. 6), a Loop Catheter 5 (FIG. 7), a Cardiac Catheter 6 with a Connector 7 at its proximal end (FIG. 8) and an Aligning device 8 (FIG. 9).

Figure 13:
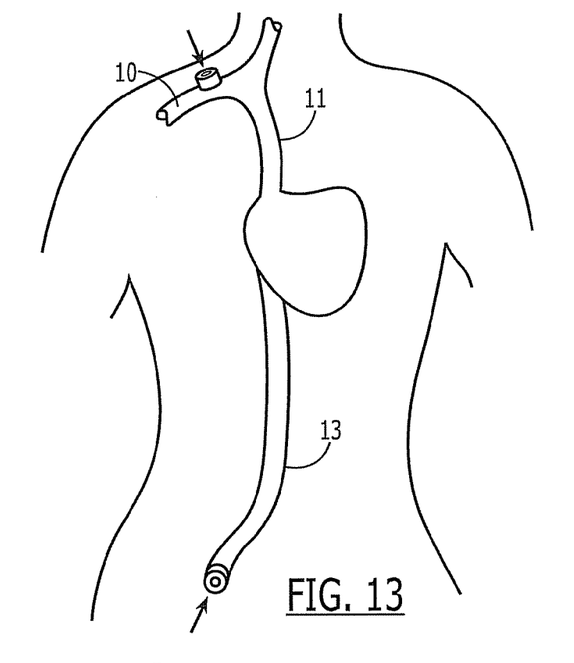
FIG. 13 is an outline of the human body showing details of the position of the catheter introducers in the subclavian vein and the femoral vein, which are identified with arrows.

Before using the elements of this invention, a puncture as needed to insert the catheter introducer in the subclavian vein 10 is performed on the patient (FIG. 13, as identified with an arrow).

Figure 14:
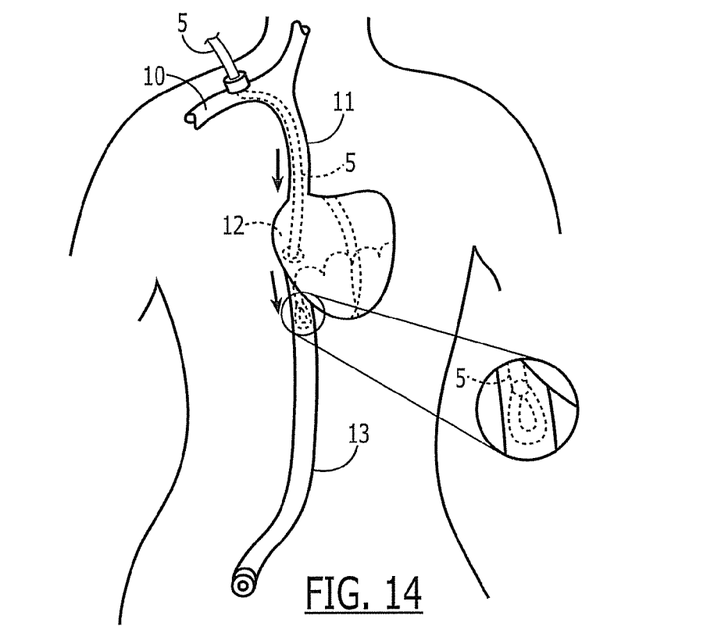
FIG. 14 is an outline of the human body showing details of the insertion of the Loop Catheter in the subclavian vein, and identifying with dotted lines the section in the superior vena cava, the right atrium of the heart, and the insertion and a short section in the inferior vena cava.

The Loop Catheter 5 of this invention is passed along the catheter introducer in the subclavian vein, and after passing along the superior vena cava 11 (FIG. 14, see the arrow), it is inserted in the right atrium 12 of the heart and passed to the inferior vena cava 13, where it moves a short section downward (FIG. 14).

Figures 15, 16:
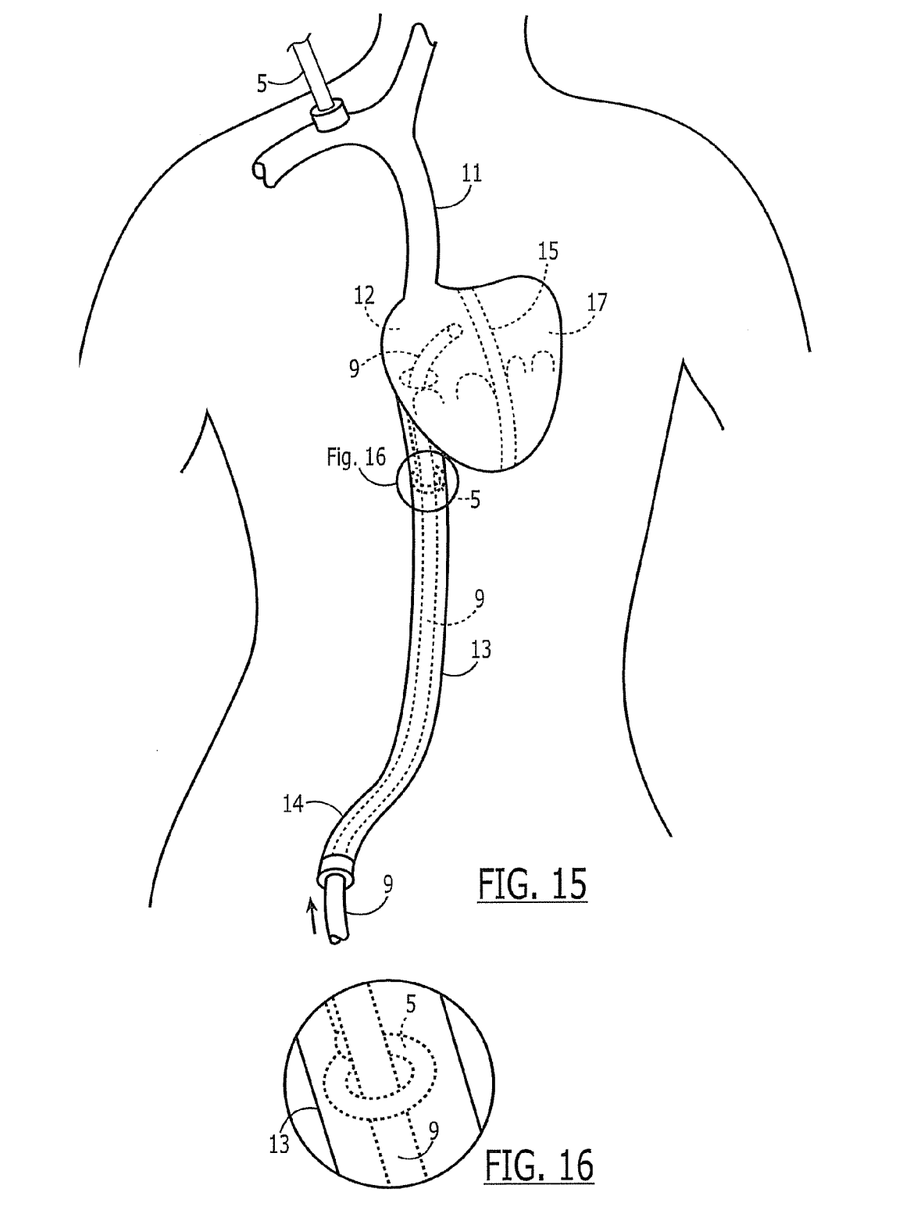
FIG. 15 is an outline of the human body showing details of the introduction of the transseptal sheath by femoral route until it reaches the right atrium of the heart as identified with dotted lines.
FIG. 16 represents an expansion circular of the FIG. 15, of the passing through the loop of the Loop Catheter in the inferior vena cava.

The transseptal sheath 9 is inserted by femoral route 14 (FIG. 15, see the arrow) by means of an appropriate introducer and passed along the inferior vena cava 13 until it reaches the right atrium of the heart 12 after passing through the loop of the Loop Catheter 5, which has been previously inserted in the inferior vena cava 13 (FIGS. 15 and 16).

Figure 17:
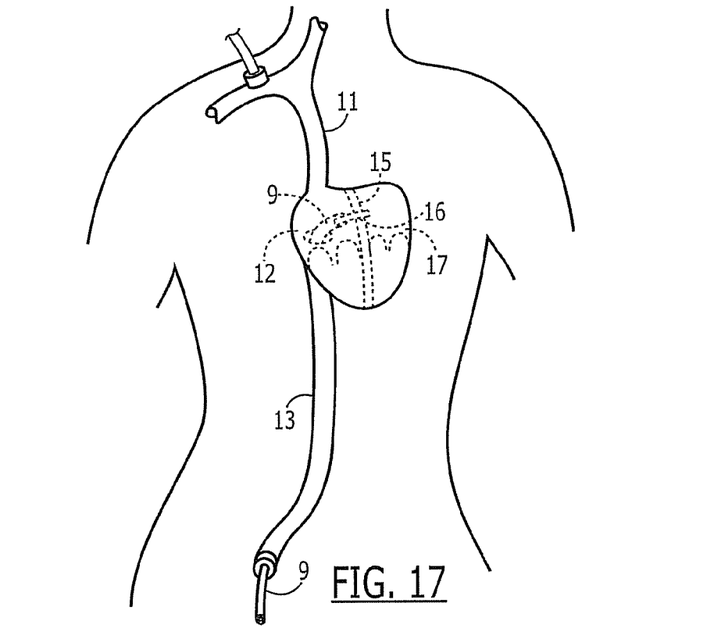
FIG. 17 is an outline of the human body showing details of the puncture performed on the interatrial septum of the heart using the Brockenbrough needle well-known method, as identified with dotted lines.

A puncture on the interatrial septum 15 is performed with a Brockenbrough needle using traditional methods, all the conventional elements being removed when the procedure finishes. Once the puncture 16 is made, the transseptal sheath 9 is passed through the puncture from the right atrium 12 to the left atrium 17 (reference being made to FIG. 17).

Figure 10:
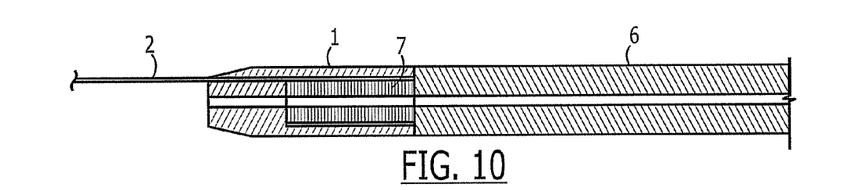
FIG. 10 is a side sectional view of the Connector (the proximal End of the Cardiac Catheter) inserted in the Fastener, and the Pulling Element between them.

The elements of this invention are used assembling the Connector 7 of the Cardiac Catheter 6 by inserting it in the pertinent hole of the Fastener 1, and fixing axially the Pulling Element 2 to the Fastener 1 (FIG. 10).

Figure 11:
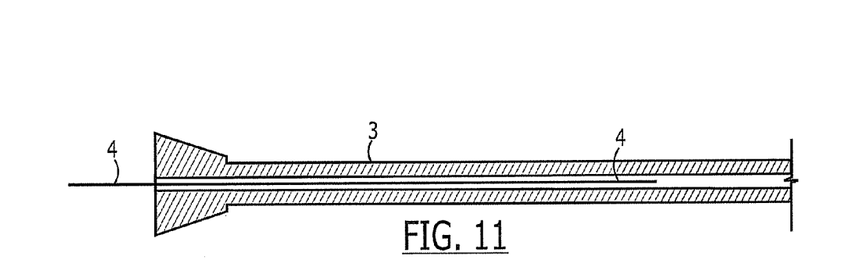
FIG. 11 is a detailed longitudinal sectional view of the Mandrel partially inserted in the Runner.
Figure 12:
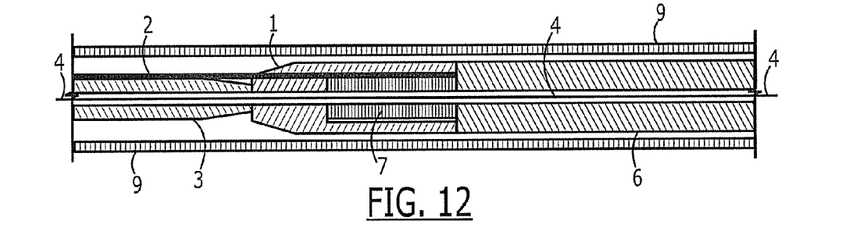
FIG. 12 is a detailed longitudinal sectional view of the same elements of FIGS. 10 and 11, now into the transseptal sheath.

The Mandrel 4 is passed through the Runner 3 (FIG. 11) and the Fastener 1, and along the central passage of the Cardiac Catheter 6 until it reaches its distal end. With this section, the Mandrel 4 conforms a unit (Kit) between the Runner 3, the Fastener 1, the Pulling Element 2 and the Cardiac Catheter 6, and keeps the Cardiac Catheter 6 unbending to let it go forward and prevent any involuntary movement. The Kit is inserted in the transseptal sheath 9 (FIG. 12).

Figure 18:
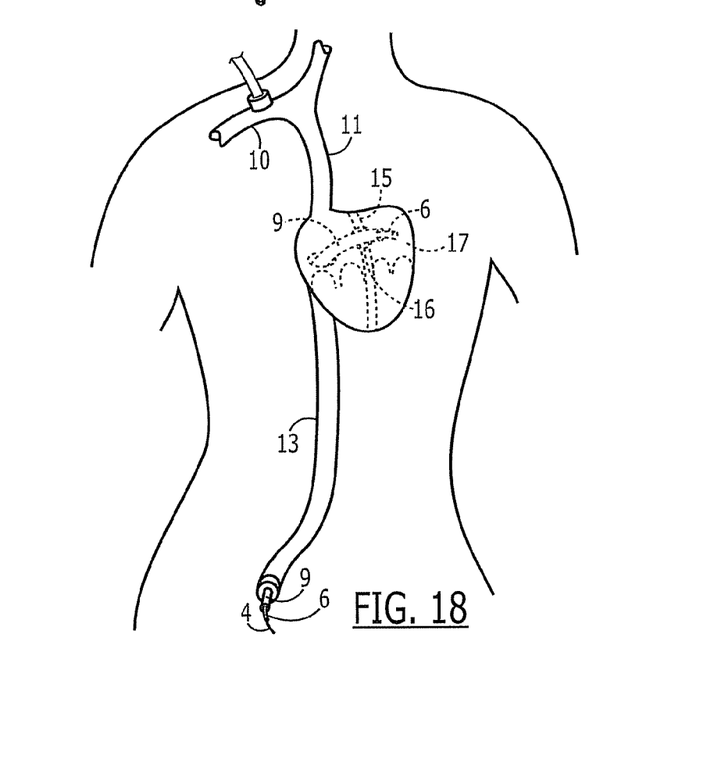
FIG. 18 is an outline of the human body showing the passage of the transseptal sheath to the left atrium, and the passage of the Cardiac Catheter having the Mandrel inside through the transseptal sheath, as identified with dotted lines.

Advancing the Runner 3 forward, the Fastener 1, the Pulling Element 2, the Mandrel 4 and the Cardiac Catheter 6 are moved through the transseptal sheath 9 until the distal end of the Cardiac Catheter 6 reaches the left atrium 17 of the heart (FIG. 18). The transseptal sheath 9 is removed from the heart to the inferior vena cava 13 and left at a short distance from the heart. During this partial removal of the transseptal sheath 9, the Mandrel 4 has an important role keeping the Cardiac Catheter 6 steady in place in the left atrium 17 (FIG. 19).

Figures 19, 20, 21:
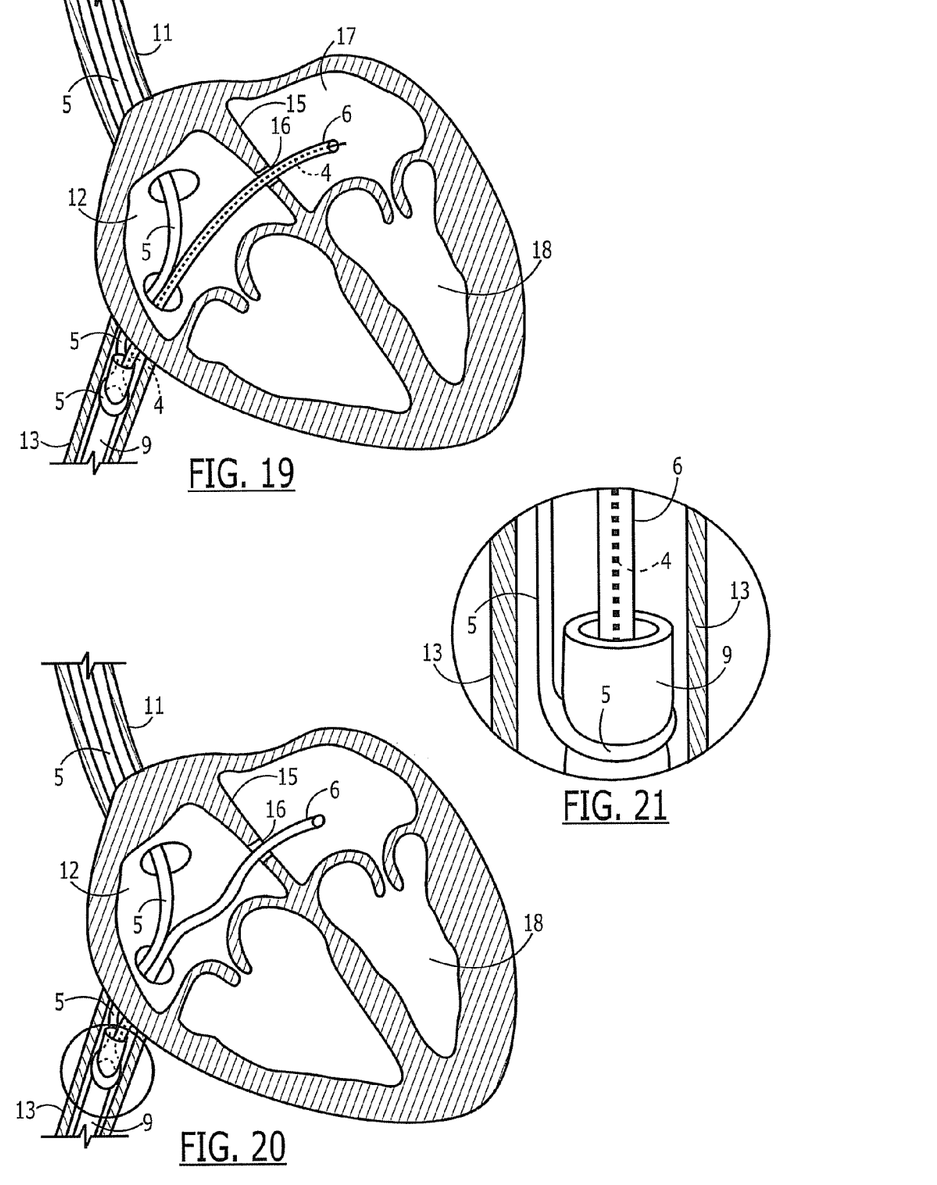
FIG. 19 is a sectional view of FIG. 1 showing details of the Cardiac Catheter having the Mandrel inside into the left atrium, and the transseptal sheath having been removed toward the inferior vena cava.
FIG. 20 is a 2-2 sectional view of FIG. 1 showing details of the Mandrel partially removed toward the proximal end of the catheter.
FIG. 21 illustrates a circled expansion of the detail of the FIG. 20, showing details, identified with dotted lines, of the Loop Catheter and this inside into the transseptal sheath.

The Mandrel 4 is removed from the distal end to the proximal end of the catheter; removing the Mandrel 4 releases the Cardiac Catheter 6, which becomes flexible (FIG. 20).

The Runner 3 continues to be advanced along the transseptal sheath 9 and the Fastener 1 is pushed until it reaches the inferior vena cava, as illustrated with reference to FIG. 20.

Figure 22:
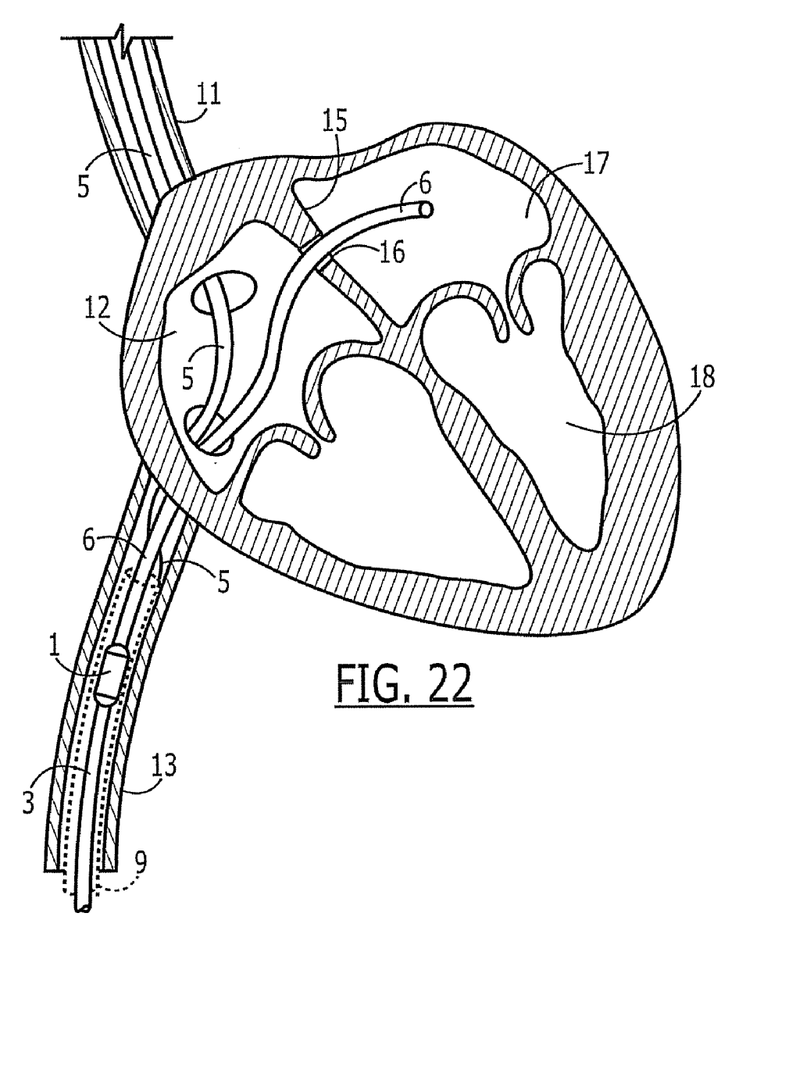
FIG. 22 is a sectional view of FIG. 1 showing details of the Runner moving inside the transseptal sheath, as identified with a dotted line, and pushing the Fastener and the Pulling Element toward the right atrium of the heart.
Figure 23:
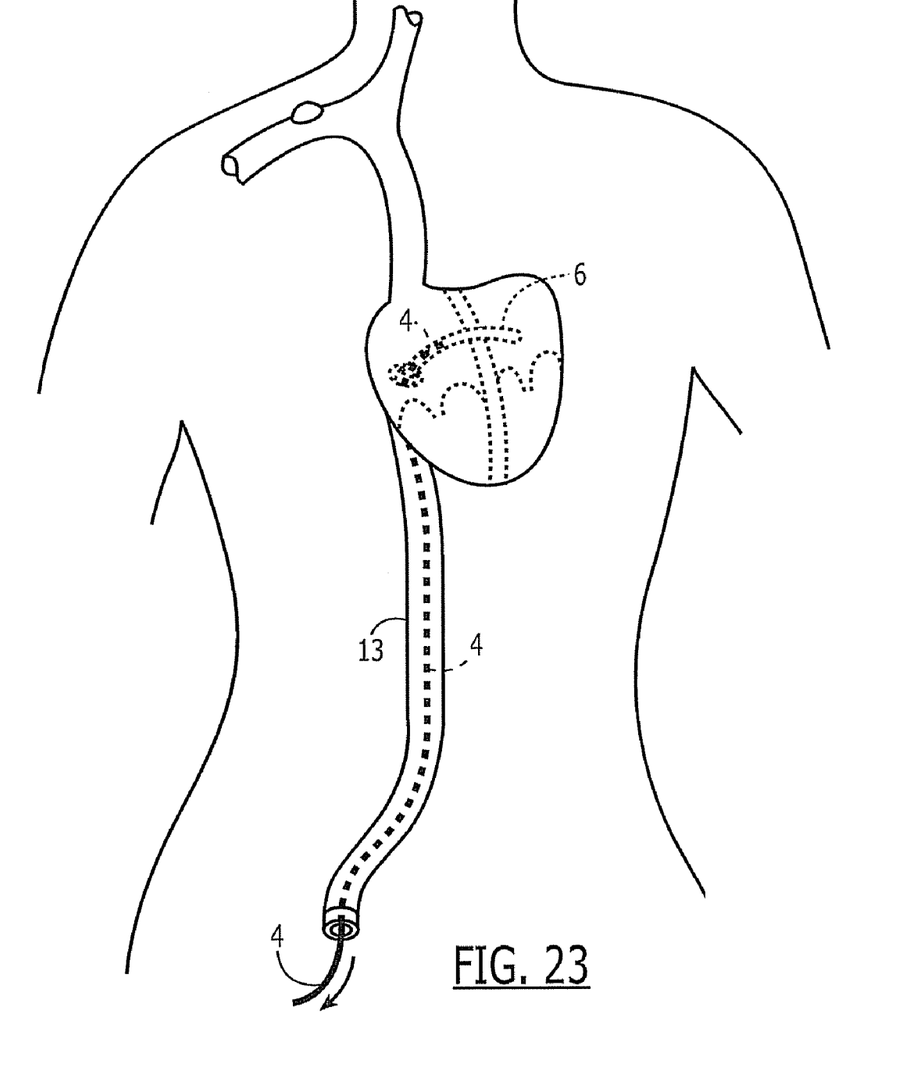
FIG. 23 is an outline of the human body showing complete retrograde removal of the Mandrel by pulling it from the proximal end of the transseptal sheath, as identified with a dotted line. The removal of the Mandrel disassembles the Fastener from the Runner, leaving the latter free inside the transseptal sheath and the former free inside the inferior vena cava.

The Mandrel 4 is completely removed from the Cardiac Catheter 6, the Fastener 1 and the Runner 3. On one hand, this procedure detaches the Runner 3, which remains inside the transseptal sheath 9; as illustrated with reference again to FIGS. 3-12. On the other hand, it leaves the proximal end of the Cardiac Catheter 6 together with the Pulling Element 2 and the Fastener 1 in the inferior vena cava of the heart as illustrated with reference to FIGS. 22 and 23.

Figure 24:
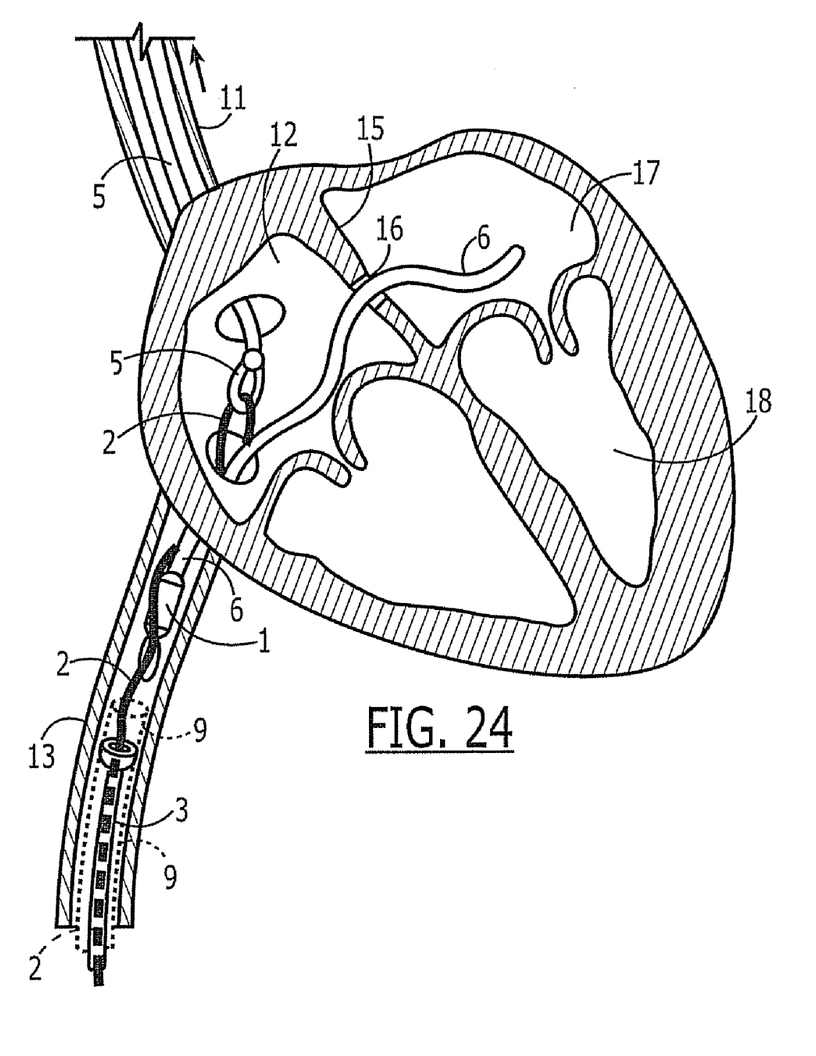
FIG. 24 is a sectional view of FIG. 1, showing details of the Loop Catheter retrograde pull of the Pulling element joined to the Fastener and the proximal end of the Cardiac Catheter, the transseptal sheath remaining inside the inferior vena cava and the detached Runner and the rest of the Pulling Element still remaining inside the transseptal sheath.
Figure 25:
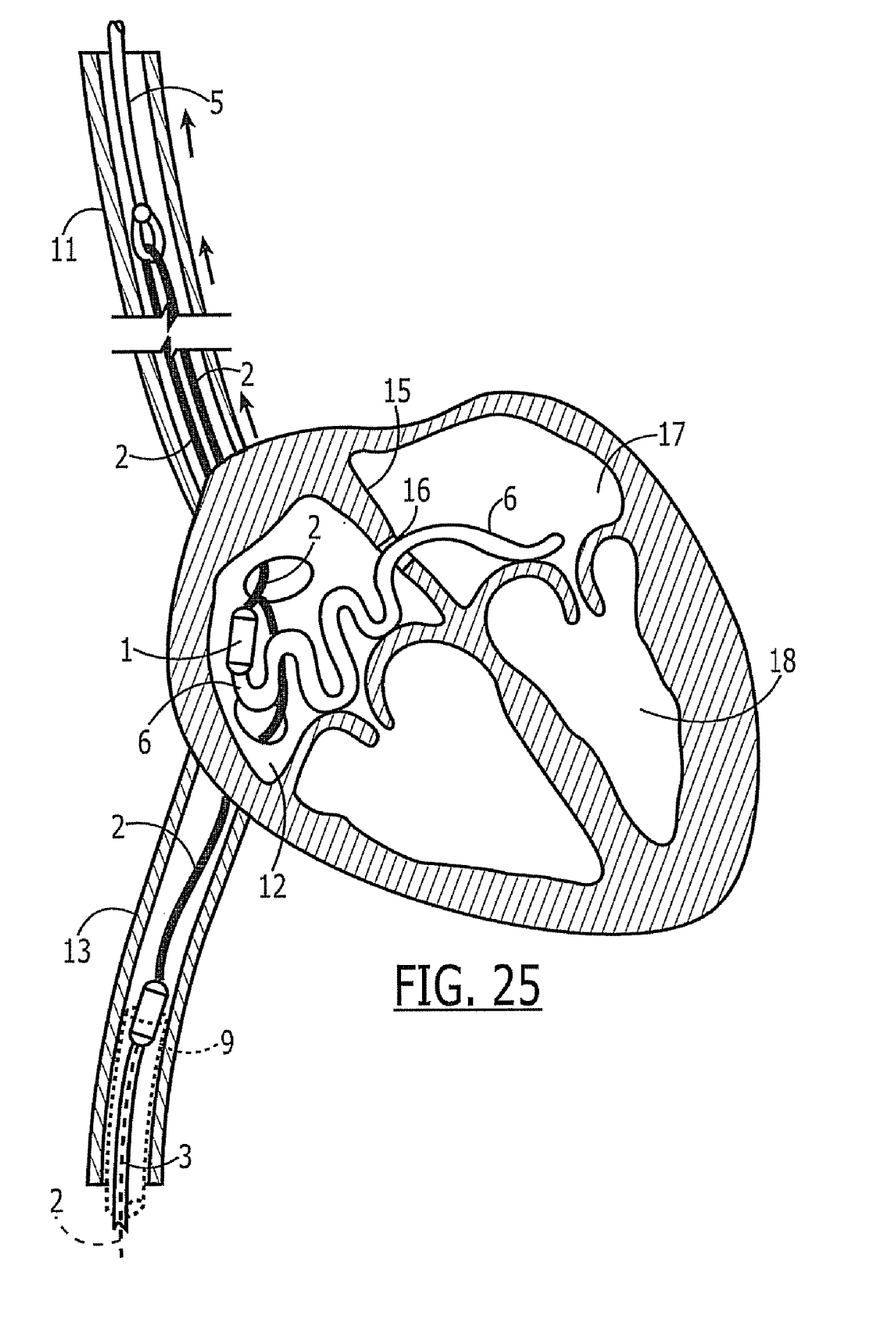
FIG. 25 is a 2-2 sectional view of FIG. 1, which has to be considered sequentially after the previous figure, showing details of the Loop 'Catheter retrograde pull of the Pulling element joined to the Fastener and the proximal end of the Cardiac Catheter inside the superior vena cava (the direction being identified with arrows), and the transseptal sheath remaining inside the inferior vena cava; the transseptal sheath is later on removed retrogradely.
Figure 26:
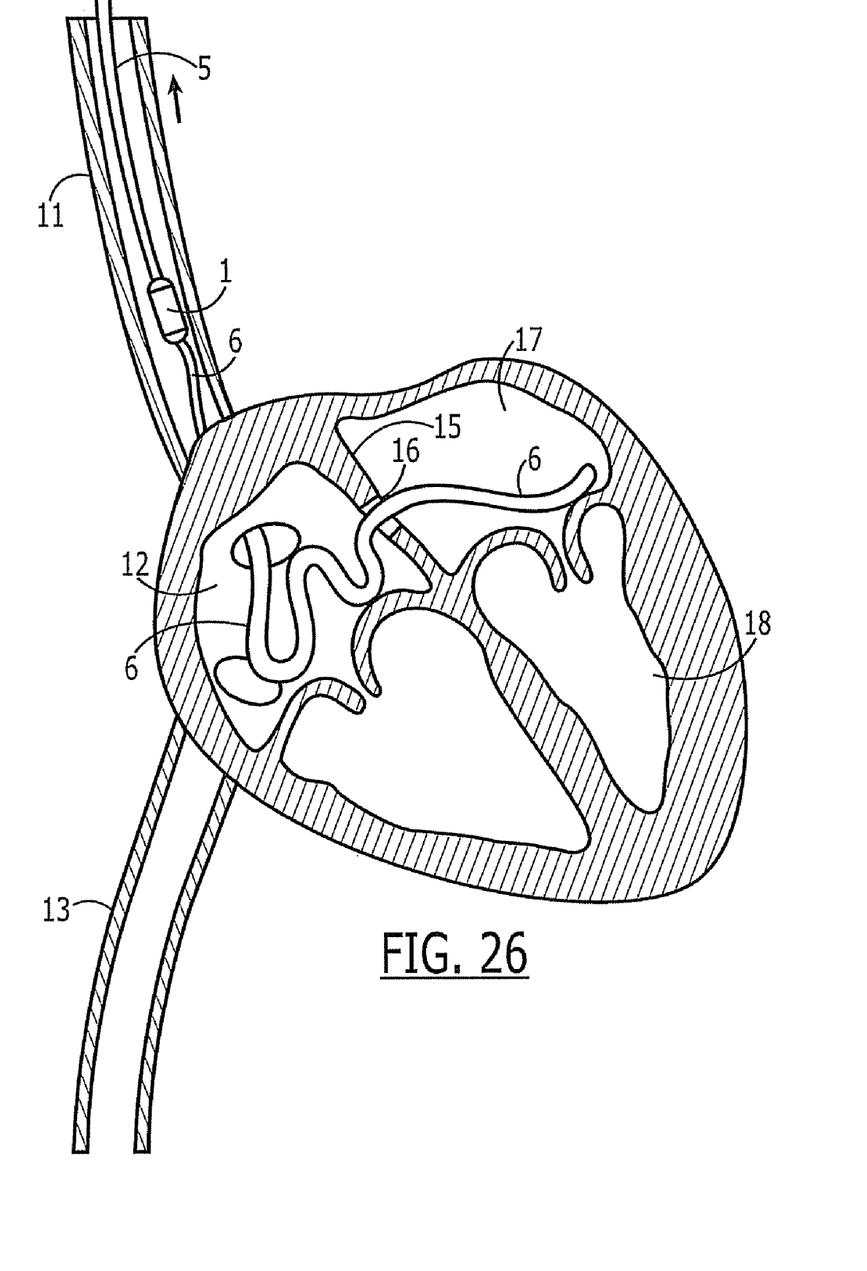
FIG. 26 is a 2-2 section view of FIG. 1, which has to be considered sequentially after the previous figure, showing details of the retrograde pull of the Fastener and the proximal End of the Cardiac Catheter by the Pulling Element into the superior vena cava.

The Loop Catheter 5 is adjusted by holding the Pulling Element 2. Removal of the Pulling Element 2 is done by means of the Loop Catheter 5 through the superior vena cava 11 as illustrated with reference to FIGS. 24, 25 and 26 until the free end of the Pulling Element 2 is taken out through the catheter introducer of the subclavian vein 10. Eventually, at operator's discretion, the Pulling Element 2 can be taken out partially and cut, and then the cut section is taken out at the site of the femoral vein.

Figure 27:
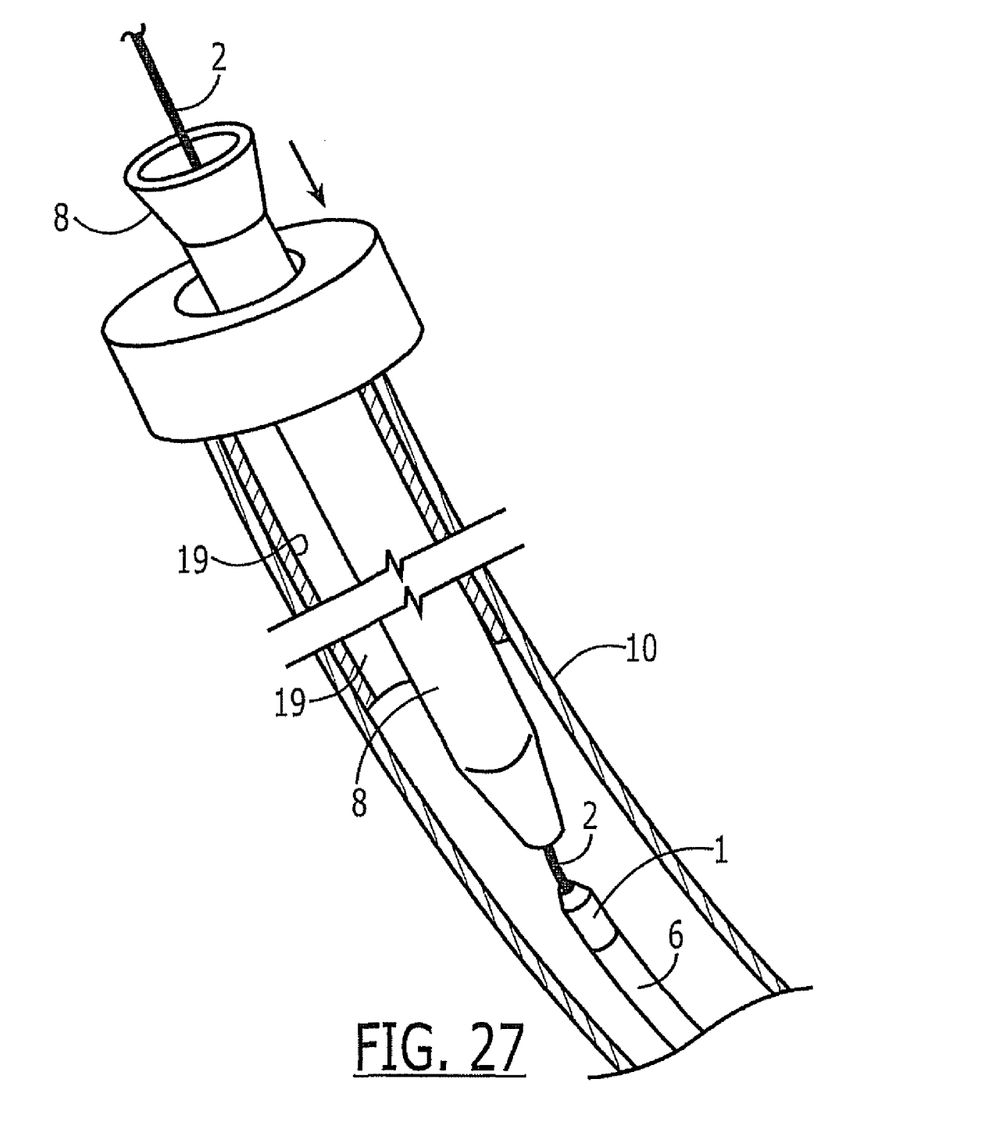
FIG. 27 is a detailed sectional view of the subclavian vein and the superior vena cava with the inner part of the catheter introducer showing the insertion of the Aligning Element inserted in the Pulling Element moving into the catheter introducer in the subclavian vein, and the superior vena cava ready to receive the Fastener and the proximal end of the Cardiac Catheter through its outlet in order to facilitate its way out through the catheter introducer.

The free end of the Pulling Element 2 is inserted in the central passage of the Aligning device 8 and then inserted in the catheter introducer 19 of the subclavian vein 10 in order to align the set composed of the Fastener 1 connected to the proximal end of the Cardiac Catheter 6 (FIG. 27) and allow its insertion in the catheter introducer of the subclavian vein 10 for smooth removal.

Figure 28:
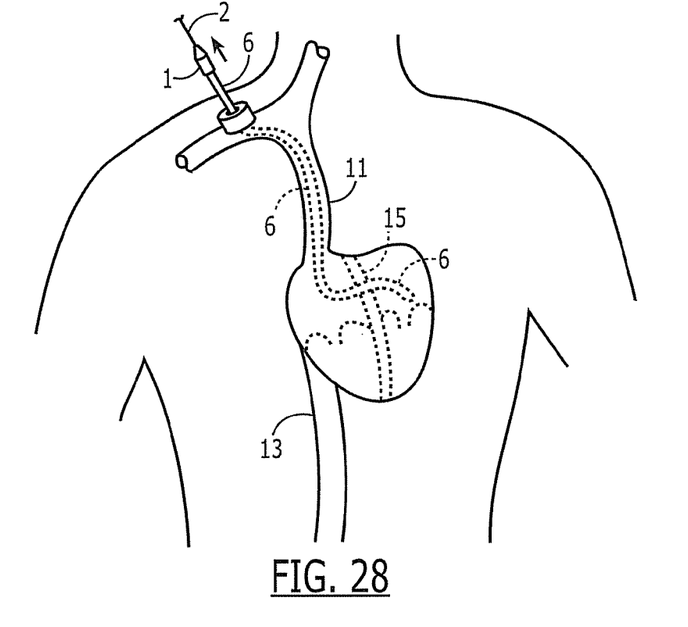
FIG. 28 is an outline of the human body showing details of the retrograde removal of the Fastener and the proximal end of the Cardiac Catheter through the catheter introducer, the localization of the other end of the Cardiac Catheter inside the superior vena cava and the left atrium or ventricle of the heart being identified with dotted lines.

The Pulling Element 2, the Fastener 1 and the proximal end of the Cardiac Catheter 6 are completely removed through the catheter introducer 19 of the subclavian vein 10, as illustrated with reference to FIG. 28.

The Fastener 1 and the Pulling Element 2 are detached from the proximal end of the Cardiac Catheter 6, and the Connector 7 of the Cardiac Catheter 6 is left uncovered.

Figure 29:
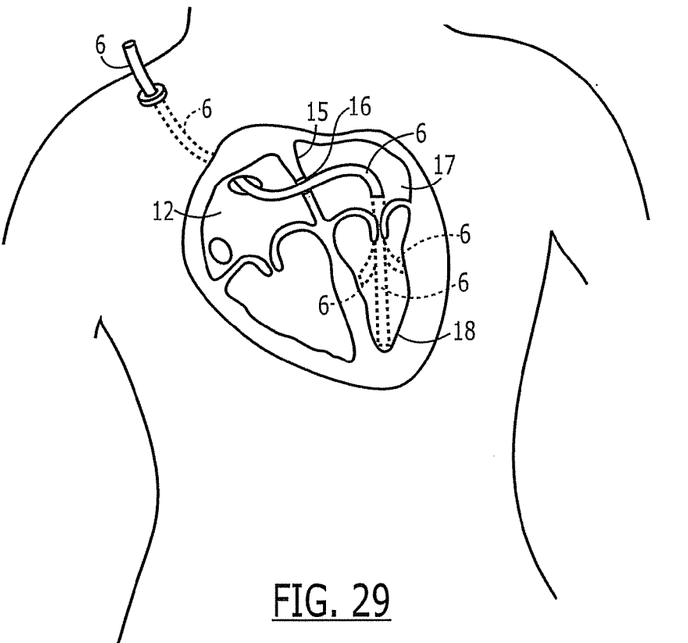
FIG. 29 is an outline of the human body, which has to be considered sequentially after the previous figure, showing details of the final position of the proximal end of the Cardiac Catheter outside the human body, and a 2-2 sectional view of the FIG. 1 showing details of the other end of the Cardiac Catheter inside the left atrial chamber, or passing through the mitral valve on different localizations in the left ventricle, as identified with dotted lines, and ready to connect the pacemaker.

Thus, the proximal end of the Cardiac Catheter 6 is left outside the human body through the subclavian vein 10, while the opposite end is inserted in the chamber of the left atrium 17 or the left ventricle 18 of the heart (FIG. 29).

The procedure finishes when the distal end of the Cardiac Catheter 6 is placed in the desired position inside the left atrium or ventricle using customary techniques, and the pacemaker or any other piece of equipment is implanted using customary procedures.

The constructive and functional advantages of this invention by which it is characterized are plain from the description above, representing a beneficial technological improvement that warrants the inclusion of the invention in the law with the pertinent legal protection as per the appended claims.

The invention claimed is:

1. A method for inserting a cardiac catheter into at least one of a left atrium and ventricle of a heart, the method comprising:
   providing a kit, the kit comprising:
      a fastener with a central passage;
      a pulling element that can be fixed to the fastener;
      a runner with a central passage;
      a cardiac catheter with a proximal end and a distal end, the cardiac catheter having a central passage, a connector having a central passage, the connector configured to fit into a corresponding hole in the fastener;
      a loop catheter with a distal loop;
      an aligning device with a central passage;
      a mandrel that can be inserted in the central passages;
   inserting the loop catheter with a first introducer into at least one of a subclavian vein and other tributary of the superior vena cava;
   passing the loop catheter from the right atrium further into the inferior vena cava;
   positioning the distal loop of the loop catheter a first distance into the inferior vena cava from the right atrium;
   inserting a trans-septal sheath with a second introducer into a femoral route;
   passing the trans-septal sheath along the inferior vena cava and through the distal loop of the loop catheter;
   puncturing an interatrial septum of the heart;
   positioning the trans-septal sheath through the interatrial puncture;
   assembling the kit to form an assembled cardiac catheter, the assembling comprising:
      inserting the connector of the cardiac catheter into the corresponding hole of the fastener;
      fixing an end of the pulling element to the fastener and leaving the other end free;
      passing the mandrel through the central passage of the runner, the central passage of the fastener, and the central passage of the cardiac catheter; and
      inserting the assembled cardiac catheter into the trans-septal sheath;
   pushing the runner in the assembled cardiac catheter along the trans-septal sheath until the distal end of the cardiac catheter reaches at least one of the left atrium and the ventricle of the heart;
   removing the trans-septal sheath from the heart and positioning the trans-septal sheath a second distance from the right atrium;
   partially removing the mandrel from the cardiac catheter by removing the mandrel from the distal end of the catheter and leaving the mandrel within the cardiac catheter at the proximal end of the cardiac catheter;
   pushing the assembled cardiac catheter until the fastener reaches the right atrium of the heart;
   completely removing the mandrel from the cardiac catheter;
   completely removing the trans-septal sheath from the femoral route;
   adjusting the loop catheter to hold the pulling element which remains in the inferior vena cava;

pulling the pulling element through the inferior vena cava, right atrium, and superior vena cava, by means of the loop catheter until the free end of the pulling elements exits the first introducer;

inserting the free end of the pulling element into the central passage of the aligning device;

inserting the aligning device into the first introducer;

pulling the pulling element and the aligning device until the fastener and proximal end of the cardiac catheter exit the first introducer; and detaching the pulling element and fastener from the connector of the cardiac catheter to leave the cardiac catheter connector uncovered and ready to be connected to an implantable device.

2. The method according to claim 1, further comprising cutting the pulling element after it exits the first introducer and removing a cut section of the pulling element from the femoral route.

3. The method according to claim 1 or 2, further comprising keeping the proximal end of the cardiac catheter outside the first introducer after it exits the first introducer while the distal end of the cardiac catheter is positioned in the left atrium or the left ventricle of the heart.

4. The method according to claim 1 or 2, further comprising placing the distal end of the cardiac catheter in any one of the multiple desired sites in the left atrium and/or left ventricle according to patient requirements.

* * * * *